United States Patent [19]
Vinson

[11] Patent Number: 6,139,860
[45] Date of Patent: Oct. 31, 2000

[54] METHOD OF STIMULATING CILIA

[75] Inventor: Gavin Paul Vinson, London, United Kingdom

[73] Assignee: Queen Mary & Westfield College, London, United Kingdom

[21] Appl. No.: 09/202,220

[22] PCT Filed: Jun. 10, 1997

[86] PCT No.: PCT/GB97/01550

§ 371 Date: Feb. 2, 1999

§ 102(e) Date: Feb. 2, 1999

[87] PCT Pub. No.: WO97/47315

PCT Pub. Date: Dec. 18, 1997

[30] Foreign Application Priority Data

Jun. 11, 1996 [GB] United Kingdom .................. 9612164

[51] Int. Cl.$^7$ .............................. A61F 2/02; A61F 13/02; A61L 9/04; A61K 9/14; A61K 9/48

[52] U.S. Cl. .............................. 424/423; 424/45; 424/46; 424/433; 424/451; 424/464

[58] Field of Search ................. 424/45, 46, 423, 424/433, 451, 464

[56] References Cited

U.S. PATENT DOCUMENTS 5,338,774  8/1994  Dudley et al. .

OTHER PUBLICATIONS

Kobayashi et al., "Angiotensin II simulates airway ciliary motility to rabbit cultured tracheal epithelium", See Abstract, 1990.

Berstein and Alexander (1992), Endocrine Reviews, vol. 13, No. 2, pp. 381–386, "Counterpoint: Molecular Analysis of the Angiotensin II Receptor".

Barker, S., et al., (1993), Journal of Molecular Endocrinology, vol. 11, pp. 241–245, "Rapid Communication".

M. E. Kervancioglu et al., (1994), Bio Cell, vol. 82, pp. 103–107, "A simple techinque for the long–term non–polarised and polarised culture of human fallopian tube epithelial cells".

R. W. Noyes, et al., (1950), Fertility & Sterility, vol. 1, No. 1, pp. 3–25, "Dating the Endometrial Biopsy".

C. De Geyter, et al.; Int. Journal of Andrology, 15, pp. 485–497 (1992).

H. Holland–Moritz and W. Krause; Int. Journal of Andrology, 15, pp. 473–485 (1992).

S.T. Mortimer and D. Mortimer, Journal of Andrology, 11, pp. 195–203 (1990).

Koyama Norihiro, Kyorin Igakkai Zasshi, vol. 24, No. 4, pp. 517–528 (1990).

Koyama Norihiro, Kyorin Igakkai Zasshi, vol. 24, No. 4, pp. 517–528 (abstract) (1993).

Mizutani et al., Andrologia 17 (2): 150–156 (1985).

Sharpe et al., J. Physiol. (London), 239(3), pp. 595–622 1974).

Kaneko et al., J. Pharm. Dyn. 7, pp. 87–93 (1983).

*Primary Examiner*—Carlos Azpuru
*Attorney, Agent, or Firm*—Fay, Sharpe, Fagan, Minnich & McKee, LLP

[57] ABSTRACT

The present invention relates to the use of angiotensin II or an analogue thereof, for the manufacture of a medicament for stimulating cilia, such as fallopian tube cilia or bronchial epithelial cell cilia. Such a medicament may be used for promoting ovarian transport thus benefitting conception, or alternatively for treating such respiratory conditions as asthma.

13 Claims, 3 Drawing Sheets

Effects of increasing concentrations of AII on fallopian tube ciliary beat frequency. Values are the mean ± SE.*, $P<0.05$, **, $P<0.01$ (by paired $t$ test).

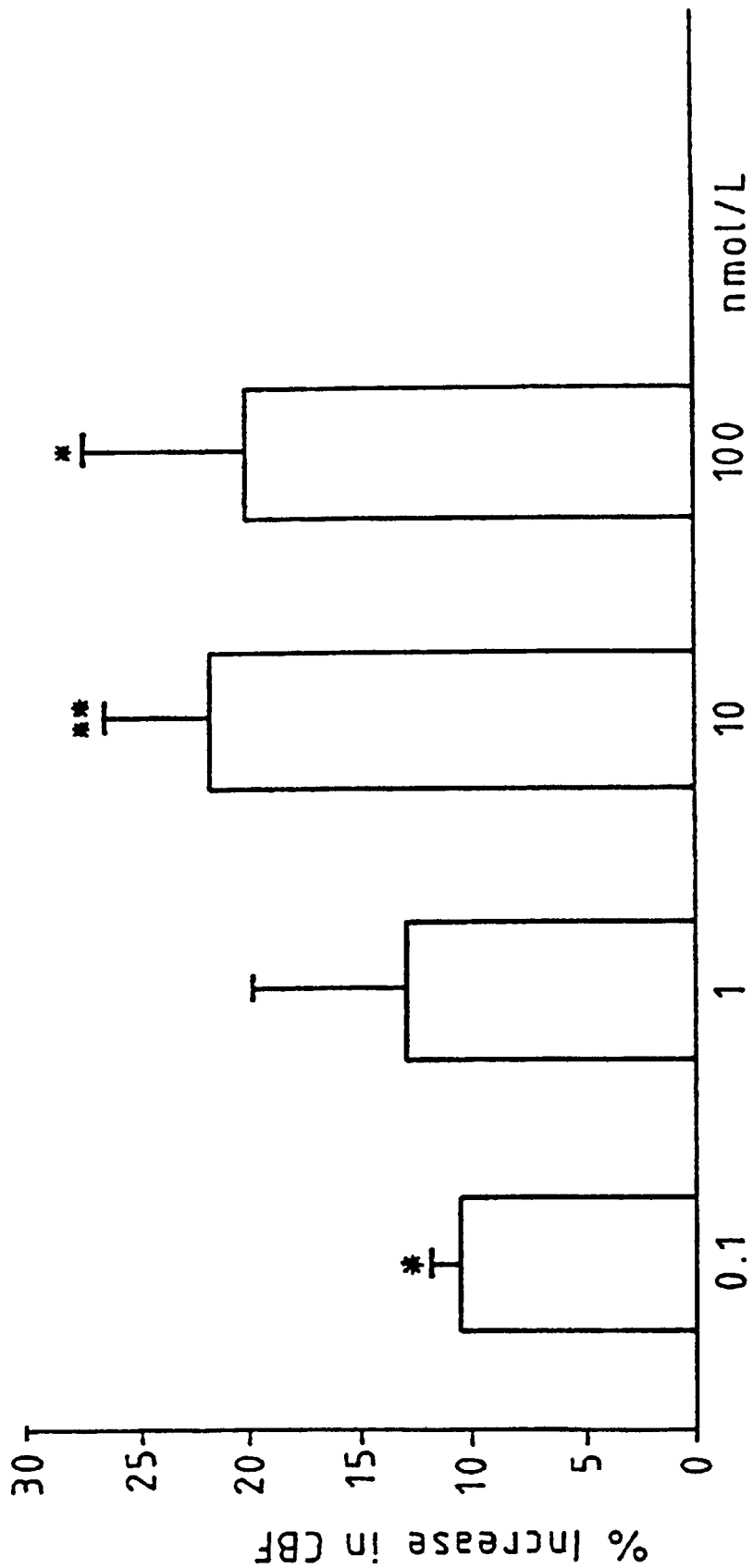
FIG.1 Effects of increasing concentrations of AII on fallopian tube ciliary beat frequency. Values are the mean ± SE. *, $P<0.05$; **, $P<0.01$ (by paired $t$ test).

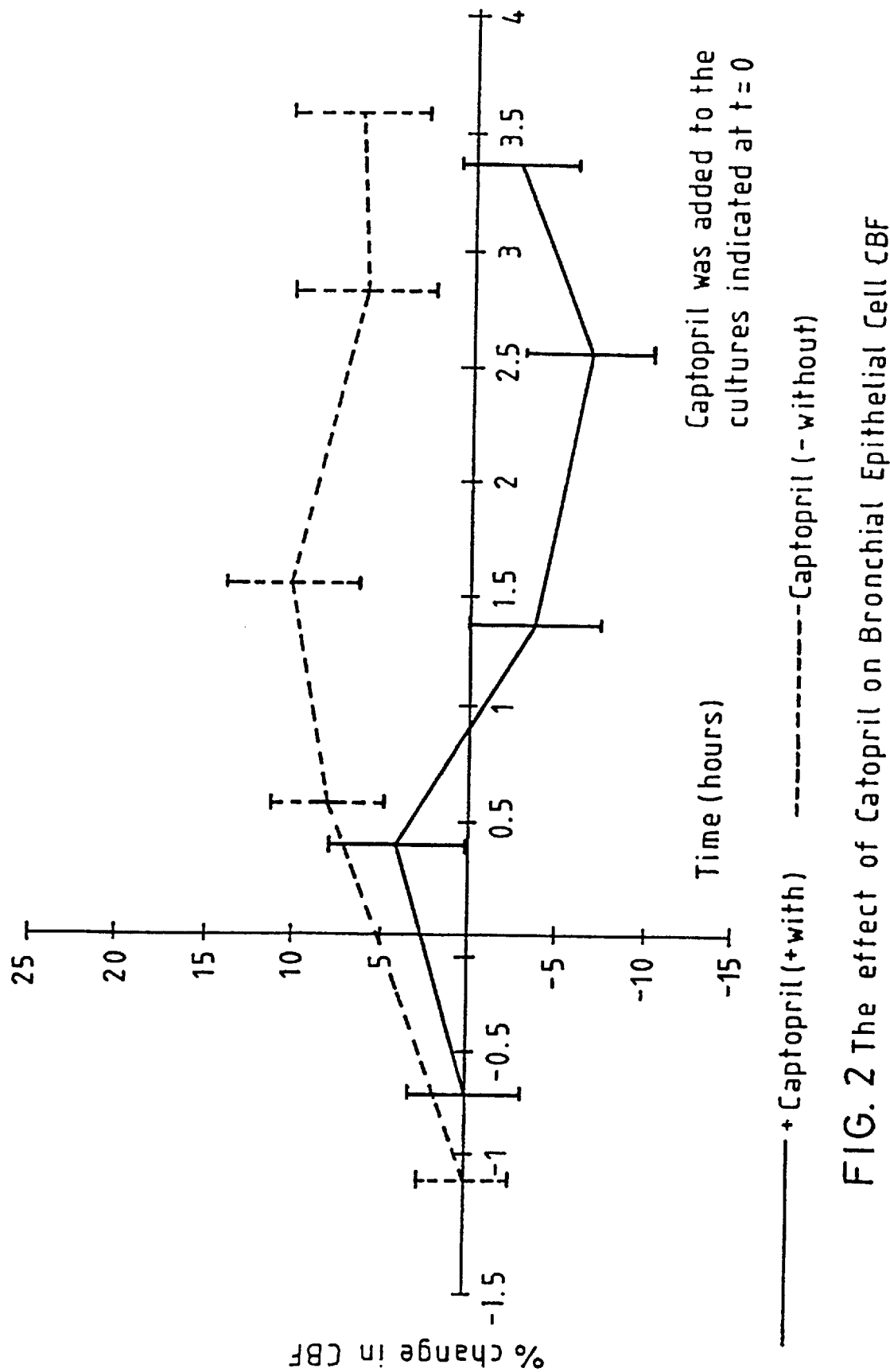
FIG. 2 The effect of Catopril on Bronchial Epithelial Cell CBF

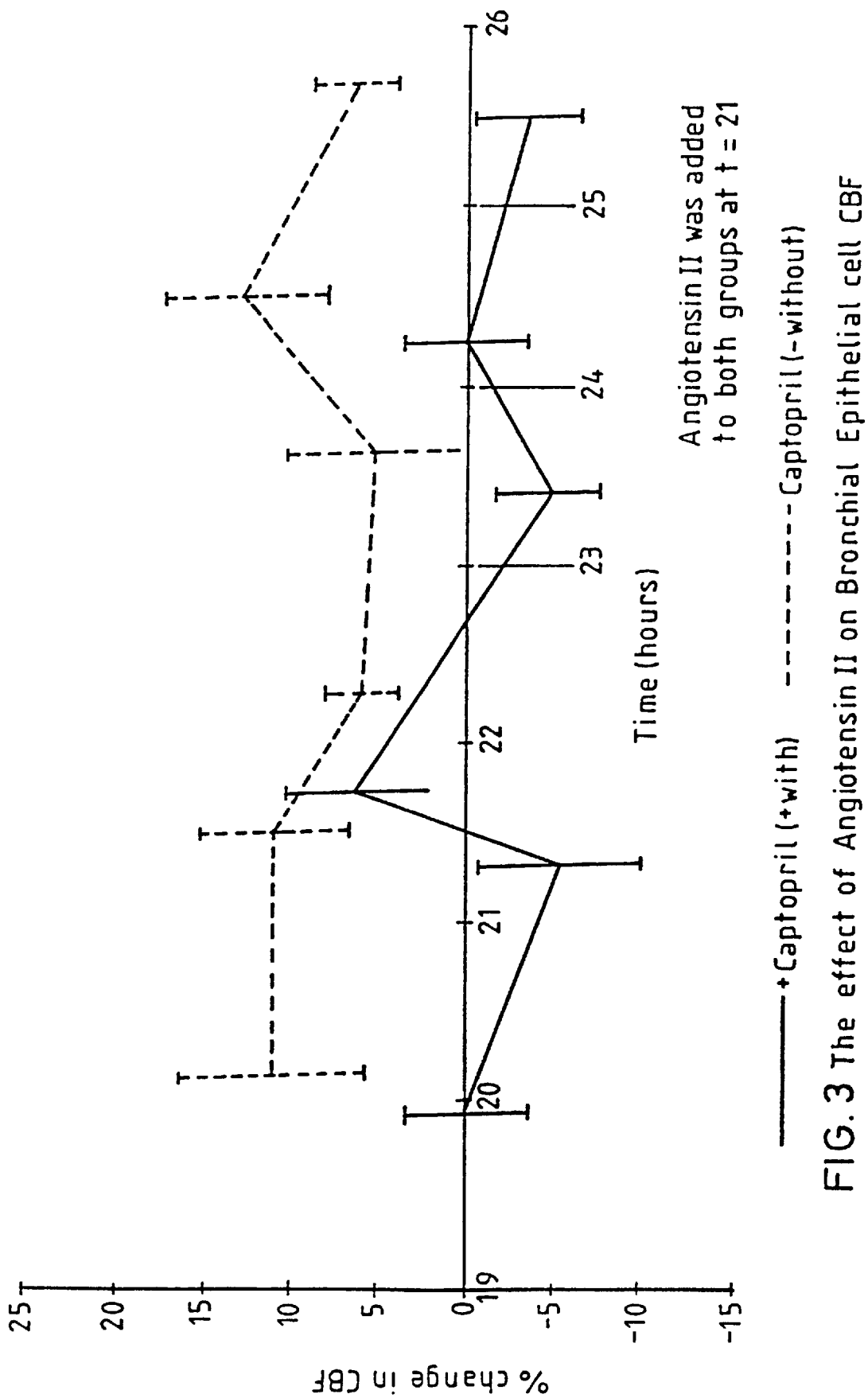
FIG. 3 The effect of Angiotensin II on Bronchial Epithelial cell CBF

METHOD OF STIMULATING CILIA

BACKGROUND OF THE INVENTION the present invention relates to the use of angiotensin II (Ang II) or an analogue thereof, for the manufacture of a medicament for stimulating cilia, such as fallopian tube cilia and cilia on the secretory epithelia of the respiratory system. In particular, it relates to the use of Ang II, or an analogue thereof, for the manufacture of a medicament for stimulating cilia thus, for example, promoting ovarian transport, particularly in humans, with a consequential beneficial effect on conception. Alternatively, the medicament may be used for treating respiratory conditions such as asthma, bronchitis, or pneumonia.

Angiotensin II is an octapeptide, usually regarded as being produced in the blood, firstly by the action of renin, an enzyme secreted by the kidney, on angiotensinogen, resulting in the formation of the decapeptide precursor, angiotensin I, and secondly the action of a dipeptidase "angiotensin converting enzyme"; this enzyme acts on angiotensin I to form angiotensin II. Angiotensin II, in turn, undergoes hydrolysis by an aminopeptidase to yield the heptapeptide angiotensin III angiotensin 1–7).

The hormone angiotensin II (Ang II) forms part of the renin—angiotensin system which helps to control electrolyte balance and blood pressure within the body. There are several tissues within the body upon which Ang II acts, they include the adrenal gland, uterus, liver, brain and kidney.

Amongst the several established functions of angiotensin II, it is known to be involved in vaso-constriction, which leads to hypertension. Most treatments for high blood pressure will include blockage of angiotensin function in one way or another. Ang II also stimulates the secretion of aldosterone by the adrenal cortex. Aldosterone is a potent hormone which acts primarily on the kidney to promote sodium retention and thus inter alia, heightens the hypertensive effects of angiotensin acting directly on the vasculature.

Ang II is known to act on various sites in the brain, and one of its actions in animals is the regulation of thirst and drinking.

Angiotensin also has trophic effects on the vasculature, promoting growth of the muscles in the arterial wall. It is also thought to be angiogenic, i.e. it causes vascularisation of newly developing tissue.

Most of the established effects of Ang II have been found to occur via the $AT_1$ subtype of the Ang II receptor, which is a seven transmembrane domain receptor. This receptor has been cloned and sequenced from a variety of tissues, and has been found to be a 359 amino acid polypeptide with a predicted molecular weight of around 40 kD (Berstein and Alexander, (1992), *Endocr. Rev.*, 13, 381–386). Studies using photo-affinity labelling and crosslinking agents have suggested molecular weights for mature receptor of approximately 65 kD and 116 kD, respectively, which may reflectively, which may reflect glycosylation of asparagine residues within the extra-cellular domain.

From the recent development of a hybridoma cell line, see Barker, S., et al, *J. Mol Endocr.*, 11, 241–245, (1993), it has been found possible to produce monoclonal antibodies to the $AT_1$ subtype of the Ang II receptor. In consequence, such receptors have been found to exist both on maturing rat and human sperm tails, and on free swimming sperm obtained by vaginal lavage from mated rats, and in human ejaculated sperm.

WO (95/01202) discloses the use of angiotensin II to promote fertilization of mammalian eggs by increasing sperm motility. In particular, it discloses that Ang II may be used to promote in-vitro fertilization.

Although Ang II receptors have been extensively studied in the ovary and uterus, there is no information on their presence and role in the fallopian tube. Indeed, the AT1 subtype has been reported as absent from the uterus, although the AT2 subtype is present. Ang II have now been located in the human fallopian tube and uterus, using monoclonal antibodies to the AT1 subtype of the Ang II receptor. In the fallopian tube, and also in the tubules of the kidney, the respiratory tract, the intestine, breast ducts, prostate gland ducts, pancreatic duct, and in blood vessels, the antibody reveals that the receptor is specifically localised in the epithelial cells (endothelial cells in blood vessels), suggesting a role for the receptor in epithelial and ductal transport. In the fallopian tube, as in the respiratory tract, its distribution specifically shows close intimacy with the cilia which these epithelial cells carry, and that therefore ciliary function may be regulated by this receptor.

The incidence of chronic respiratory disease has shown a significant increase in recent years. There seems little doubt that much of this is associated with atmospheric pollution. Currently such chronic conditions are treated in a variety of palliative ways. Though generally valuable, few of these treatments directly address mucociliary clearance. This mechanism is a major natural defence system for the whole respiratory tract, which removes potentially harmful material through the co-ordinated beat of the cilia in a mucous blanket. Factors affecting the clearance rate therefore include the rheological properties of the mucous itself, as well as the beat frequency of the cilia. The means by which these properties are regulated under normal physiological conditions is largely unclear, though ciliary action is known to be affected by a number of factors. These include neurotransmitters and their agonists and antagonists, and the intracellular signal molecules, cyclic AMP, and calcium ions.

SUMMARY OF THE INVENTION

The present invention relates to a method of stimulating cilia to increase the ciliary beat frequency comprising administering an effective amount of angiotensin II or a salt or analog thereof to an animal.

BRIEF DESCRIPTION OF THE DRAWINGS

FIG. 1 is a plot showing the effects of increasing concentration of angiotensin II on fallopian tube ciliary beat frequency (CBF);

FIG. 2 is a plot showing the effect of catopril on bronchial epithelial cell CBF; and FIG. 3 is a plot showing the effect of angiotensin II on bronchial epithelial cell CBF.

DETAILED DESCRIPTION OF THE INVENTION

It has now been found that Ang II, or an analogue thereof, has a stimulatory action on fallopian tube cilia beat frequency (CBF), and on bronchial epithelial cell cilia beat frequency and these compounds may therefore have similar stimulatory effect upon the cilia at the locations mentioned above.

This newly discovered property of Ang II enables it to be used to promote ovum transport through the fallopian tube in women who are unable to conceive, or are having difficulty in conceiving. Whilst women with no fallopian tube ciliary activity may get pregnant, since ciliary activity is one of the mechanisms responsible for ovum transport, the stimulatory action of Ang II will help to promote conception.

In addition, Ang II may be used to promote mucociliary clearance, thus alleviating the distressing symptoms of asthma, or other bonichial disease.

According to one aspect of the invention there is provided the use of angiotensin II or a salt or analogue thereof for the manufacture of a medicament for use in stimulating cilia, in particular for increasing ciliary beat frequency, preferably fallopian tube ciliary beat frequency, and bronchial epithelial cell ciliary beat frequency.

According to a second aspect of the invention there is provided the use of angiotensin II or a salt or analogue thereof for the manufacture of a medicament for promoting ovum transport in a fallopian tube.

According to another aspect of the invention there is provided the use of angiotensin II or a salt or analogue there of for the manufacture of a medicament for alleviating asthma, or other bronchial disease.

Analogues of Ang II which may be used for stimulating cilia i.e. increasing ciliary beat frequency, include Ang II amide, angiotensin III (Ang 1–7) and angiotensin IV (Ang 3–8).

The medicament may be a formulation made up as a tablet, capsule, syrup, injectable solution, suppository, pessary, sprays, inhalers, slow release implant or cream, which may be applied topically or internally via for example the vagina, rectum, mouth or nose. Such formulations could thus be administered orally, intramuscularly, intravenously, rectally, intranasally or vaginally. In the case of bronchial disease treatment, one preferred form for the medicament formulation is an aerosol for inhalation.

Excipients which may be incorporated within such formulations include carriers, binders, stabilizers, preservatives and flavours. Examples of suitable excipients which may be incorporated into the formulations include a binder such as gum tragacanth, acacia, corn starch or gelatin; an excipient such as microcrystalline cellulose; a disintegrating agent such as corn starch, pregelatinized starch, alginic acid and the like; a lubricant such as stearic acid or magnesium stearate; a sweetening agent such as sucrose, lactose or saccharin; a flavouring agent such as orange, peppermint, oil of wintergreen or cherry. When the formulation is a capsule, it may contain, in addition to materials of the above type, a liquid carrier such as fatty oil. Various other materials may be present as coatings or to otherwise modify the physical form of the formulation. For instance, tablets may be coated with shellac, sugar or both. A syrup or elixir may contain the active compound, sucrose as a sweetening agent, methyl and propyl parabans as preservatives, a dye and a flavouring such as cherry or orange flavour.

According to a third aspect of the invention there is provided a method of stimulating cilia, in particular a method of increasing ciliary beat frequency, preferably fallopian tube ciliary beat frequency, or bronchial epithelial cell ciliary beat frequency comprising administering an effective amount of angiotensin II or a salt or analogue thereof to an animal, preferably a human.

According to yet another aspect of the invention there is provided a method of promoting ovum transport in a fallopian tube comprising administering an effective amount of angiotensin II or a salt or analogue thereof to an animal, preferably a human.

The invention will be further described with reference to the following example:

EXAMPLE 1

Fallopian Tube Ciliary Beat Frequency (CBF) Studies

Fallopian tubes were obtained from woman undergoing sterilization or hysterectomy for benign conditions after obtaining informed consent and local ethical committee approval. A venous blood sample was taken immediately before the operation for FSH, LH, estradiol ($E_2$) and progesterone measurements to determine hormonal status, which was confirmed by histological examination of the endometrium using criteria described by Noyes et al, 1950, *Fertil. Steril.* A, 3–25. In a subgroup or normal, ovulatory women with proven fertility, the menstrual cycle was dated by detection of LH surge in a daily specimen of venous blood and/or early morning urine. None of the patients were receiving hormone replacement therapy or talking oral contraceptives. After removal fallopian tubes were immediately transported to the laboratory in MEM-Earle's containing 1.82 U/mL heparin, 50 µg/mL streptomycin, 100 IU/mL penicillin, and 10 mmol/L HEPES and prepared as previously described (Kervancioglu et al, 1995, *Biol Cell*, 82, 103–107). Briefly, tissue was cut open and rinsed twice for any visible evidence of blood. The mucosal folds of the ampullary segment were dissected free, cut into 1-mm$^3$ pieces, and these placed in the same culture medium without heparin or HEPES. All ciliary beat frequency (CBF) experiments were carried out at room temperature. A piece of mucosa was placed in a 60×15 Falcon tissue culture dish (Becton Dickinson, Rutherford, N.J.) containing 1 mL culture medium. Ciliary activity was observed under in Olympus inverted microscope (keymed, Essex, UK) and recorded on video tapes for up to 30-min periods. Experiments showed that stable CBF was achieved within 3 min. Recordings were made beginning 5 min after the addition of any reagent. Each tissue explant provided both a control and a stimulated reading. Ang II was used at concentrations from 0.1–100 nmol/L in the presence or absence of Losartan (1000 nmol/L or CGP42112B (1000 nmol/L). The recordings were analyzed using a CE-1 enhancer (Brian Reece Scientific Instruments, Newbury, UK) which increased the contrast of the video signal so that it was possible to visualize the cilia on a television monitor. The CBFs of six different cells were determined over a period of 1 min. The position of individual cilia was fixed on the screen by means of a cross-hair light sensor, and differences in light intensity resulting from ciliary motion at the cross point of the sensor were analyzed by the use of a computer incorporating a PCX1 Video Digitiser Card (version 7.11) and Cell Tracek 8 software (Brian Reece Scientific Instruments). The differences in light intensities were computed in Hertz units. The average of six measurements from one explant was used for calculations, and data from six premenopausal women were compared for statiscal analysis.

Results

CBF was stimulated by Ang II at nanomolar concentrations; higher concentrations of Ang II did not increase CBF further (FIG. 1) When the data from all experiments using different concentrations of Ang II were combined (Table 1), there was a significant increase in CBF after the addition of Ang II to the culture medium (by ANOVA) P=0.0046), which was inhibited by the presence of losartan (by ANOVA, P=0.1176, Ang II plus losartan vs. control). CGP42112B has no inhibitory action (by ANOVA, P=0.0186, Ang II plus CGP42112B vs. control).

TABLE 1

Control and stimulated values for CBF

|  | Control | Stimulation | P value (by ANOVA) |
| --- | --- | --- | --- |
| Ang II | 6.37 ± 0.21 | 7.24 ± 0.21 | 0.0046 |
| Ang II + losartan | 6.48 ± 0.22 | 7.02 ± 0.25 | 0.1176 |
| Ang II + CGP42112B | 6.52 ± 0.27 | 7.47 ± 0.27 | 0.0186 |

Values are the mean ± SE.

Losartan: $AT_1$ receptor specific antagonist

CGP42112B: type 2 specific Ang II receptor antagonist

Conclusion

The data clearly demonstrate Ang II has a stimulating action on fallopian tube CBF. This effect was achieved at nanomolar concentrations of Ang II, further increases in the concentration of Ang II were without additional effect.

EXAMPLE 2

Nasal and bronchial tissue samples were obtained from surgical patients under the care of the E.N.T. Department and Cardiothoracic Department at St Bartholomew Hospital, respectively.

Immediately after resection the tissue samples were placed in 20 ml of cold basic media in an Universal tube and returned to the laboratory within 30 minutes of its removal. The samples were then processed as follows:

1. Tissue samples were sterilized by performing 2–3 washes in fresh basic media.
2. The samples when washed were placed in Falcon Primeria culture dishes (Becton-Dickinson Ltd, Oxford) containing 5 ml of basic media and the epithelial tissue was dissected off using sterile forceps and sterile disposable scalpel. (Swann Morton, Sheffield). As the tissue sections were dissected off they were placed in culture dishes containing fresh basic media.
3. These pieces of tissue were then further divided into smaller pieces of 1–2 $mm^3$ in size.
4. Primary cell cultures were set up by plating out three of the small pieces of tissue from the previous step in 60×15 mm Style, Falcon Primeria culture dishes (Becton-Dickinson, Lincoln Park, N.J.) containing 1.5 ml of culture medium with Fetal Calf Serum.
5. The cultures were incubated in a CO2 Incubator 220 Flow Laboratories, (UK) at 37=A7C and aerated with a gas blend of 5% CO2 in air.

Measurements of CBF were made using a modification of the Analogue Contrast Enhancement Technique (ACET). In this technique a COHU solid state camera was coupled to an Olympus IMT-2 inverted microscope (Olympus optical Co., UK) incorporating the Hoffman Modulation Contrast optical system (Modulation Optics Inc., Greevale, N.Y.), used to view the cells. Images from the microscope were fed onto a monitor via the COHU solid state video camera and CE-1 contrast enhancer. In the process the image undergoes electronic stretching which increases the contrast so the cilia can be observed. Ciliary beating leads to fluctuations in light intensity that are detected by a mouse-operated cross-hair light sensing probe positioned over selected ciliated cells An on-line computer with a PCX Video Digitiser Card (Brian Reece Scientific Instruments, Newbury) then calculates the CBF using the data from the probe.

When CBF measurements were made, six areas from each culture (which were in duplicates) were randomly chosen and the CBF of healthy cells measured the CBF values from 30 second scans were performed over each of the selected areas. For experimental purposes the explants were removed aseptically with forceps before the start of the experiments. The medium of all cultures were changed and preliminary CBF measurements made. Following these measurements the media was again changed to culture media containing Captopril and/or Angiotensin II. Control cultures had their media changed without additions. The cultures were then incubated for 5 to 10 minutes before measurements of CBF were recommended.

Results

Bronchial epithelial cell cultures were used. Captopril, 10 micromoles per liter, was added to the group indicated. By an hour after the addition of the Captopril there was a clear difference between the two groups. The CBF of the group exposed to Captopril fell below its baseline measurement as indicated by the percentage change in CBF. (see FIG. 2) The group that was not dosed with Captopril in contrast showed a rise in CBF (FIG. 2). The difference between the groups persisted to the start of the next stage of the experiment.

After the addition of angiotension II, CBF values for the group dosed with Captopril increased. (see FIG. 3)

Conclusion

The results show that, as in other tissues, bronchial epithelial cells are capable of generating angiotensin II endogenously.

The addition of angiotensin converting enzyme inhibitor limits the endogenous production of the active hormone. As a consequence ciliary beat frequency is inhibited and is only restored with the addition of endogenous angiotensin II.

What is claimed is:

1. A method of using angiotensin II (Ang II) or a salt or analogue thereof for the manufacture of a medicament for stimulating cilia, the medicament increasing fallopian tube ciliary beat frequency.

2. A method of using angiotensin II Ang II or a salt or analogue thereof for the manufacture of a medicament for promoting ovum transport in a fallopian tube.

3. A method of using angiotensin II Ang II or a salt or analogue thereof for the manufacture of a medicament for the treatment of asthma.

4. The method according to claim 1 wherein the Ang II analogue is selected from the group consisting of Ang II amide, angiotensin III, and angiotensin IV.

5. The method according to claim 1 wherein the medicament is formulated into at least one of a tablet, capsule, syrup, injectable solution, suppository, pessary, spray, inhaler, slow release implant or cream.

6. A method of promoting ovum transport in a fallopian tube, comprising administering an effective amount of angiotensin II or a salt or analogue thereof to an animal.

7. A method of treating asthma comprising administering an effective amount of angiotensin III or a salt or analogue thereof to an animal.

8. A method according to claim 6 wherein the animal is a human.

9. A method according to claim 7 wherein the animal is a human.

10. The method according to claim 2 wherein the Ang II analogue is selected from the group consisting of Ang II amide, angiotensin III, and angiotensin IV.

11. The method according to claim 3 wherein the Ang II analogue is selected from the group consisting of Ang II amide, angiotensin III, and angiotensin IV.

12. The method according to claim 2 wherein the medicament is formulated into at least one of a tablet, capsule, syrup, injectable solution, suppository, pessary, spray, inhaler, slow release implant or cream.

13. The method according to claim 3 wherein the medicament is formulated into at least one of a tablet, capsule, syrup, injectable solution, suppository, pessary, spray, inhaler, slow release implant or cream.

* * * * *